United States Patent
Nurmi et al.

(10) Patent No.: US 6,756,490 B2
(45) Date of Patent: Jun. 29, 2004

(54) METHOD OF CRYSTALLIZING MALTITOL

(75) Inventors: Juha Nurmi, Kirkkonummi (FI); Olli-Pekka Eroma, Kotka (FI); Heikki Heikkilä, Espoo (FI); Johanna Nygren, Virkkala (FI)

(73) Assignee: Danisco Sweeteners Oy, Espoo (FI)

( * ) Notice: Subject to any disclaimer, the term of this patent is extended or adjusted under 35 U.S.C. 154(b) by 0 days.

(21) Appl. No.: 10/332,826

(22) PCT Filed: Jul. 10, 2001

(86) PCT No.: PCT/FI01/00658

§ 371 (c)(1),
(2), (4) Date: Jun. 16, 2003

(87) PCT Pub. No.: WO02/04473

PCT Pub. Date: Jan. 17, 2002

(65) Prior Publication Data

US 2004/0039194 A1 Feb. 26, 2004

(30) Foreign Application Priority Data

Jul. 12, 2000 (FI) .............................. 20001655

(51) Int. Cl.[7] .......................... C07H 15/04; C07H 1/06

(52) U.S. Cl. ..................... 536/4.1; 536/18.5; 536/124; 536/127; 127/61

(58) Field of Search ................. 536/4.1, 18.5, 536/124, 127; 127/61

(56) References Cited

U.S. PATENT DOCUMENTS

| | | | | |
|---|---|---|---|---|
| 4,408,041 A | * | 10/1983 | Hirao et al. | 536/4.1 |
| 4,717,765 A | * | 1/1988 | Hirao et al. | 536/124 |
| 4,846,139 A | * | 7/1989 | Devos et al. | 127/40 |
| 4,849,023 A | | 7/1989 | Devos et al. | |
| 5,304,388 A | | 4/1994 | Ueno et al. | |
| 5,494,525 A | | 2/1996 | Heikki et al. | |
| 5,651,829 A | | 7/1997 | Caboche | |

FOREIGN PATENT DOCUMENTS

| | | | |
|---|---|---|---|
| EP | 0 202 165 A1 | | 5/1986 |
| EP | 0 937 733 A2 | | 1/1999 |
| EP | 0937733 | * | 1/1999 |
| JP | 06234786 | | 8/1994 |
| WO | WO 98/50589 | | 11/1998 |

* cited by examiner

Primary Examiner—James O. Wilson
Assistant Examiner—Michael C. Henry
(74) Attorney, Agent, or Firm—Scully, Scott, Murphy & Presser

(57) ABSTRACT

The invention relates to a method of crystallizing maltitol from a maltitol solution by supersaturating the solution in repsect of maltitol and crystallizing the maltitol from the solution. In the process of the invention, the maltitol-containing solution is brought to a supersaturated state, and the solution is subjected to evaporation, until a crystallization mass is obtained which has a crystal yield of 1 to 80% on maltitol, and a dry solids content of over 50%. After bringing the solution to a supersaturated state, the solution is preferably seeded by adding maltitol seed crystals. In one embodiment of the invention, additional feed liquid is added during the crystallization by evaporation.

30 Claims, No Drawings

METHOD OF CRYSTALLIZING MALTITOL

BACKGROUND OF THE INVENTION

The invention relates to a novel method of preparing anhydrous crystalline maltitol.

Maltitol (α(1→4)glucosylsorbitol) is a sugar alcohol generally used as a sweetening agent in low-caloric, dietary and low-cariogenic foods, such as confectionary products and chewing gums. Maltitol has a sweet taste similar to that of sugar, and the sweetening power of crystalline maltitol with high purity has a sweetness of about 85 to 95% of that of sucrose, making it sweeter than all other polyols except xylitol.

Maltitol is produced from a starch solution, which is first enzymatically hydrolyzed into maltose syrup. After purification and concentration, the maltose syrup is catalytically hydrogenated to maltitol. Following additional purification steps to remove the starting materials and the catalyst, the solution is concentrated to a syrup and then the maltitol syrup (containing more than 50% maltitol) is crystallized. The maltitol syrup used as the starting material for crystallization also contains low levels of sorbitol, maltotritol and higher hydrogenated oligosaccharides.

Maltitol in dry form is extremely hygroscopic and deliquescent. As a rule, maltitol has been considered very difficult to prepare in anhydrous crystalline form, e.g. due to its viscosity and solubility characteristics.

A process for preparing anhydrous crystals of maltitol has been described for the first time in U.S. Pat. Nos. 4,408,041 and 4,717,765 (Hayashibara Co.). In this process, an aqueous maltitol solution having a maltitol content of at least 65% (supersaturation degree of about 1.05–1.50) is subjected to crystallization at a temperature in the range of 0–95° C. The supersaturation degree and viscosity of the solution can be regulated by adding a water-soluble organic solvent, e.g. methanol, ethanol and acetone. Crystallization of the solution is started at a temperature of about 40–95° C. and in a supersaturated concentration, and the content is simultaneously cooled gradually with gentle stirring to obtain a massecuite containing anhydrous crystals of maltitol. The presence of seed crystals in an amount of 0.1–20.00% can accelerate the crystallization. The massecuite thus obtained is then separated into anhydrous crystals of maltitol and mother liquor by conventional separation methods. The method produces anhydrous crystals of maltitol, having a melting point of 146.5–147.0° C.

U.S. Pat. No. 4,846,139 (Roquette Frères) discloses a first industrial process for preparing pure maltitol. In this process, the crystallization of maltitol is carried out by cooling crystallization.

U.S. Pat. No. 5,304,388 (Ueno Seiyaku Oyo Kenkyulo Co.) discloses a method of manufacturing powdery or granular crystalline maltitol. In this method, seed crystals of maltitol (e.g. at a temperature of 105° C.) are first added to an aqueous solution of maltitol having a moisture content of 1–15% by weight (temperature e.g. 90° C.). The mixture is subjected to kneading in the presence or absence of an additive selected from the group consisting of a fat, an oil and a surface-active agent, and a shearing force is continuously applied to the kneaded mass. By applying a shearing force to the kneaded mass, powdery crystalline maltitol can be obtained continuously and at a high yield. In this process, the crystals are not separated from the mother liquor. The product is impure and does not fulfill the requirements of a high quality crystalline product.

U.S. Pat. No. 4,849,023 (Roquette Frères) discloses a method where crystalline maltitol is manufactured from a concentrated maltitol syrup with a 90% dry matter content by maintaining the maltitol syrup four hours at a temperature of 75° C., after which spontaneous nucleation starts. The crystallization vessel is then cooled to a temperature of 25° C. The crystal mass is drained by centrifugation, and the crystals are dried on a fluidized bed. A crystalline maltitol product is obtained with a yield of 63% and a purity of 99.2% (by HPLC).

In accordance with U.S. Pat. No. 5,651,829 (Roquette Frères), crystalline maltitol can be obtained from a maltitol syrup which has a dry matter content of at least 50% and exhibits a maltitol concentration greater than or equal to 92% by finely atomizing this syrup on a moving pulverulent bed of particles of crystallized maltitol at a concentration which is at least equal to that of the syrup, the bed having a temperature of between 60 and 110° C.

European Patent Application EP 0 937 733 A2 (Hayashibara) discloses a continuous method of manufacturing anhydrous crystalline maltitol, where seed crystals are added by mixing to a concentrated solution of maltitol with heating to give a seed crystal-containing massecuite, and the massecuite thus obtained is subjected to disintegration, mixing, stirring and transfer in an atmosphere in which the temperature and moisture are adjusted to cause crystallization to proceed. The last step may be carried out e.g. with hot air having a temperature between 70 and 100° C.

In the known crystallization methods described above, the crystallization of maltitol is effected, for example, by cooling, applying shearing forces or drying the massecuite. The typical disadvantages of the cooling-crystallization methods relate to the unfavorable supersaturation gradient between the crystallization mass and heat transfer surfaces. The viscosity and supersaturation are high close to the heat transfer surfaces Heat transfer coefficient is reduced and harmful nucleation is easily generated if cooling is fast. As a result, the crystal mass thus obtained is very difficult to centrifuge. The method is uneconomical, because only a small amount of maltitol is recovered in one step due to the solubility limits. In addition, crystallization rate is low at low temperatures, and crystal size distribution cannot be controlled.

As regards other sugars and sugar alcohols, WO 98/50589 (Xyrofin Oy) discloses a boiling crystallization method of recovering xylose. This reference describes a method of crystallizing xylose where a xylose-containing solution is evaporated to supersaturation at a boiling point of 40 to 80° C. of the solution, the solution is seeded, and the evaporation is continued at the boiling point of the crystallization mass, until a crystallization mass with a crystal yield of 1 to 60% and a dry solids content over 70% is obtained.

WO 92/16542 (Xyrofin Oy) discloses a process for the preparation of crystalline anhydrous lactitol by bringing an aqueous lactitol solution to supersaturation in respect of lactitol, and subjecting the solution to crystallization conditions at a temperature above 70° C., by evaporating the solution or lowering the temperature under simultaneous stirring, whereupon crystalline anhydrous lactitol is formed. A boiling crystallization method has thus been proposed as one alternative for preparing crystalline lactitol.

Boiling crystallization methods for maltitol have not been suggested in the prior art, obviously because it was not expected that the boiling crystallization could be applied to the crystallization of maltitol, due to the very poor crystallization properties of maltitol. Only crystallization-bycooling methods have been proposed for the separation of pure maltitol crystals from an impure mother liquid.

BRIEF DESCRIPTION OF THE INVENTION

The object of the present invention is to provide a method of manufacturing anhydrous crystalline maltitol by a simple procedure and with high efficiency.

In order to achieve the above-mentioned object, there is provided, according to the present invention, a method of manufacturing anhydrous maltitol using a boiling crystallization method. The method of the invention proved feasible for producing high purity crystals from maltitol syrups having varying purity and varying oligosaccharide contents.

DETAILED DESCRIPTION OF THE INVENTION

The present invention relates to a method of crystallizing maltitol from a maltitol solution by supersaturating the solution in respect of maltitol and crystallizing the maltitol from the solution.

The method of the invention is characterized in that the maltitol-containing solution is brought to a supersaturated state, and the solution is subjected to crystallization by evaporation until a crystallization mass is obtained which has a crystal yield of 1 to 80% on maltitol, and a dry solids content of over 50%.

Preferably, a crystallization mass is obtained which has a crystal yield of 30 to 80%, most preferably 50 to 80% on maltitol, and 65 to 70% on dry solids.

The crystal yields of maltitol above refer to yields immediately after boiling.

The maltitol-containing solution can be obtained e.g. from a starch hydrolysate by methods known per se, including hydrolysis, hydrogenation of maltose to maltitol, and purification e.g. by chromatography or ion-exchange.

The maltitol-containing solution used as the starting material contains preferably at least about 85%, more preferably at least about 88% by weight of maltitol on dissolved dry solids. In the most preferred embodiment of the invention, the maltitol solution contains at least about 92% by weight of maltitol on dissolved dry solids.

The maltitol-containing solution used as the starting material has typically an oligosaccharide (e.g. maltotritol) content less than 4% by weight on dissolved dry solids.

In a preferred embodiment of the invention, the matitol-containing solution is brought to a supersaturated state by evaporation. Preferably, the solution is evaporated to a dry solids content of 80 to 90% by weight. The evaporation is conveniently carried out at the boiling point of the solution at a low pressure, e.g. at 120 to 140 mbar. The evaporation temperature may vary within the range of 50 to 100° C., preferably within the range of 55 to 70° C.

To form maltitol crystals from a supersaturated solution, seeding is employed. In a preferred embodiment of the invention, seeding is effected by adding seed crystals to the supersaturated solution. As seed crystals, it is possible to use a particulate maltitol powder, typically anhydrous maltitol seed crystals. The amount of seed crystals is preferably 0.001 to 1% by weight of particulate maltitol, based on the maltitol of the crystallization mass, depending e.g. on the size of the seed crystals.

Seeding may also be carried out by using any other known seeding methods, without adding maltitol seed crystals. Seeding may be effected using spontaneous seeding or ultrawave seeding, for example.

Seeding is carried out at a point where a suitable supersaturation has been achieved. As a rule, a suitable seeding supersaturation is within the range of 1.05 to 1.3.

The crystallization by evaporation (after seeding) in accordance with the present invention is conveniently carried out at the boiling point of the solution, under a low pressure. As a rule, the crystallization is carried out at a temperature of 50 to 100° C., preferably at a temperature of 55 to 70° C. The supersaturation of the solution in respect of maltitol during the crystallization is preferably 1.05 to 1.3. During crystallization by evaporation, the apparent viscosity of the crystallization mass is within the range of 5 to 200 Pa.

During the crystallization by evaporation, the crystal suspension is subjected to boiling and evaporation until a sufficient degree of crystallization (yield, reduction in maltitol purity of the mother liquor, and crystal size) has been achieved. The crystallization by evaporation is usually continued for 1 to 15 hours. During this time, it is possible to achieve a maltitol yield of 1 to 80%, preferably 50 to 80% (crystal yields of maltitol immediately after boiling), and a crystal size of 0.05 to 0.5 mm.

The pH in the crystallization is typically within the range of 4 to 11. During the crystallization by evaporation, the crystal mass is preferably mixed.

In one embodiment of the invention, additional feed liquid is added to the maltitol solution simultaneously with the crystallization by evaporation in order to raise the level of the maltitol solution in the crystallizer and to raise the dry substance content of the maltitol solution. The additional feed liquid can be added continuously or batchwise.

In another embodiment of the invention, the maltitol-containing solution is cooled simultaneously with the crystallization by evaporation (after seeding). In the combined boiling-and-cooling process, the temperature is typically dropped to a temperature which is 10 to 20° C. lower than the seeding point temperature. A typical cooling rate is 1° C./h to 5° C./h.

When the crystallization by evaporation is terminated, the crystal mass is advantageously mixed without cooling. Mixing is preferably carried out under atmospheric pressure at a temperature of 50 to 100° C., preferably at a temperature of 55 to 70° C. Mixing is conveniently continued for 0.5 to 30 hours.

Alternatively, when the crystallization by evaporation is terminated, the temperature of the crystallization mass is preferably dropped to a range of 70 to 20° C. Usually, cooling is effected for 10 to 30 hours. Preferably, cooling is effected to a temperature of 50 to 30° C., and especially to 45 to 40° C. As a rule, the cooling rate is 1° C./h to 5° C./h.

If necessary, the supersaturation of the crystallization mass is reduced by raising the temperature and/or diluting the crystallization mass with water or a maltitol-containing solution, so that the viscosity of the crystallization mass drops sufficiently for effective separation of crystallized material. Typically, the viscosity of the crystallization mass is then 50 to 200 Pa.

The crystals can be separated, for example, by centrifugation, filtration, decantation etc., preferably by centrifugation. After the separation step, the crystals are dried, e.g. with hot air. The maltitol content of the crystal fraction obtained is typically over 95%.

In the process of the present invention, the temperature and supersaturation gradient between the heat carrier surface and the crystallization mass is advantageous. The temperature in the vicinity of the heat carrier surfaces is high. Any small crystals may grow, and formation of any new crystal nuclei can be avoided, unlike in the crystallization by cooling. The rate of crystallization is high, since the temperature is suitable and the viscosity of the mother liquor is low, i.e. mass and heat transfer is efficient because of boiling.

The method of the invention makes it very easy to control the crystal size. Also, better output (kg crystals/m³ crystallization mass/h), improved yield and better crystal quality are achieved. Surprisingly, centrifugation of the mass is easy, both by using a batch centrifuge and a continuous centrifuge.

In the specification and the claims, supersaturation of a solution (apparent supersaturation) in respect of maltitol means a dimensionless ratio of the measured maltitol content to the solubility of maltitol, the ratio being calculated from the equation:

$$s = \frac{\text{malatitol content in solution}}{\text{solubility of maltitol at the same temperature}}$$

where s is supersaturation, and the unit of measurement for the maltitol content and maltitol solubility is g/100 g of water. Also, the terms 'supersaturated' and 'supersaturation' refer to the saturation of the solution in respect of maltitol.

Preferred embodiments of the invention will be described in greater detail by the following examples, which are not to be construed as limiting the scope of the invention.

The following analyses were made of the crystallization samples:

RDS: refractometric dry substance (based on pure maltitol), weight-%.

DS: dry substance with Karl Fischer titration, weight-%.

Colour measured from filtered (0.2 µm membrane) 10% solution; pH 5, 420 nm, 4 cm tube (ICUMSA method).

HPLC (for the determination of carbohydrates): $Na^+$-column; 0.6–0.8 ml/min, T=85° C.

DSC (Differential Scanning Calorimeter): 30° C.–>200° C., 10 ° C./min.

Moisture: Moisture from the crystals was analysed by coulometric Karl Fischer titration, weight-%.

In the specification and in the attached claims, maltitol purity refers to the proportion of maltitol in the dry solids contained in the solution or mixture. The purity is indicated as % by weight unless stated otherwise.

EXAMPLE 1

The maltitol-containing feed liquid to be treated was prepared from crystalline xylitol and maltitol. A total of 180 liters of feed syrup having DS of 52% and a temperature of 60° C. was made. The feed liquid contained 88% of maltitol, based on the dry solids content. The feed liquid was added to a 400-liter boiling crystallizer, and the evaporation was started at a temperature of 60° C. and at a pressure of 125 mbar. The boiling liquid was seeded with 150 ml of a seed suspension (150 g of milled maltitol crystals in 500 ml i-propanol; mean particle size of the crystals 0.03 mm) at RDS of 80.8, at a temperature of 60° C. and at a pressure of about 125 mbar. The viscosity of the liquid at the seeding point was about 200 cP. After seeding, the boiling crystallization was continued for 3 hours at a temperature of 60 ° C. and at a pressure of 125 mbar, by simultaneously adding new feed liquid to the maltitol solution. A 75-liter batch of the mass obtained by boiling crystallization (RDSmass 89.0 and RDSml 79.0) was mixed at 60° C. overnight (15 hours) and centrifuged. (ROSmass refers to DS of the mass expressed as % by weight and RDSml refers to DS of the mother liquid expressed as % by weight). Crystallization yield before centrifugation was 62% of maltitol (53.5% of DS) corresponding to 71.4% mother liquid purity. The final average crystal size was 0.3 mm.

Centrifugation was carried out with a batch centrifuge (basket diameter 0.4 m; 3 min at 1800 rpm), with different amounts of washing water. The centrifuge was loaded with about 13 kg of crystal mass in one centrifugation. The crystals obtained after centrifugation were dried in a co-current drum drier with air (having an inlet temperature of about 90° C.). The purity of the seeding sample and combined run-off of the centrifuging tests (washing with 0.2, 0.8 and 1.7 liters of water) as well as the purity of the crystals (HPLC $Na^+$) expressed as % of DS are set forth in the following table:

|  | Maltitol % of DS |
| --- | --- |
| Seeding sample | 86.7 |
| Combined run-off | 74.3 |
| Crystals; 0.2-liter wash | 98.0 |
| Crystals; 0.8-liter wash | 98.8 |
| Crystals; 1.7-liter wash | 99.0 |

The centrifugation yield was 56% of maltitol (48.2% of DS) calculated from the purity values.

EXAMPLE 2

2134 g of a maltitol syrup having a maltitol content of 95.7%, a maltotritol content of 2.3% and a sorbitol content of 1.5% was evaporated to RDS of 77.2% using a Rotavapor R-153 evaporator. The syrup was moved to 2-liter reaction vessel at a temperature of 60° C. The syrup was brought to the boiling point using vacuum. Seeding (at 60° C., in a supersaturation of 1.15) as made to the boiling syrup using 0.06% seeds on DS (milled Roquette Maltisorb P200 mixed with feed syrup). The seeded syrup was kept boiling under vacuum for 2.5 hours. A sample of the mass was centrifuged (a Hettich Rotina 48RSC centrifuge, 3500 rpm, 5 minutes) to determine the crystal content. The centrifuging yield after 3 hours boiling was 68.6% on DS and 70.4% on maltitol. The crystal size was 220–270 µm.

The rest of the mass was kept at 60° C. overnight. After 22 hours from seeding the centrifuging without wash gave 98.6% on DS cake and 90.6% on DS run-off purity, which corresponds to a 67.5% maltitol yield. The crystal size was 240–500 µm.

Purity of the cake centrifuged with 10% wash was 99.4% on DS. The content of the impurities was 0.6% maltotritol on DS. The colour of the cake was under 10 ICUMSA. Moisture content of the dried crystals was 0.07%. DSC-gram showed a peak at 148.8° C.

EXAMPLE 3

2154 g of a maltitol syrup having a maltitol content of 96.5%, a maltotritol content of 2.7% and a sorbitol content of 0.5% was evaporated to RDS of 77.1% and moved to a 2-liter reaction vessel at a temperature of 60° C. The syrup was brought to the boiling point using vacuum. Seeding (at 60° C., in a supersaturation of 1.15) was made to the boiling syrup with 0.06% seeds on DS. The seeded syrup was boiled under vacuum for 4.3 hours. The centrifuging yield after 4.3 hours boiling was 78.0% on DS and 79.0% on maltitol.

The mass was kept at 60° C. overnight. After 23 hours from seeding, the centrifuging without wash gave 98.4% on DS cake and 91.6% on DS run-off purity, which corresponds to a 73.8% maltitol yield. The crystal size was 150–250 μm.

Purity of the cake centrifuged with a 10% wash was 98.3% on DS. The impurities were 1.4% maltotritol on DS and 0.2% sorbitol on DS. The colour of the cake was under 10 ICUMSA. The moisture content of the dried crystals was 0.24%. DSC-gram showed a peak at 148.1° C.

EXAMPLE 4

Combined Boiling and Cooling 2491 g of a maltitol syrup having a maltitol content of 95.7%, a maltotritol content of 2.3% and a sorbitol content of 1.5% was evaporated to RDS of 80% and moved to a 2-liter reaction vessel at a temperature of 70° C. The syrup was brought to the boiling point using vacuum. Seeding (at 70° C., in a supersaturation of 1.21) was made to the boiling syrup using 0.10% seeds on DS. The seeded syrup was boiled under vacuum for 0.9 hours at 70° C. A cooling program from 70° C. to 60° C. during 3 hours was started. After 2.3 hours of boiling, the mass DS was 88.1% and the supersaturation was 1.41. The mass looked white and full of crystals. The centrifuging yield after 2.3 hours boiling was 65.8% on DS and 67.5% on maltitol.

The mass was slowly cooled to 62° C. overnight. After 2 hours from seeding, the centrifuging without wash gave 98.5% on DS cake and 91.4% on DS run-off purity, which corresponds to 62.7% maltitol yield.

Purity of the cake centrifuged with 10% wash was 99.4% on DS. The impurities were 0.5% maltotritol on DS and 0.1% sorbitol on DS. The colour of the cake was under 10 ICUMSA. The moisture content of the dried crystals was 0.05%. DSC-gram showed a peak at 149.3° C.

EXAMPLE 5

Combined Boiling and Cooling 2097 g of a maltitol syrup having a maltitol content of 96.4%, a maltotritol content of 2.7% and a sorbitol content of 0.5% was evaporated to RDS of 79.9% and moved to a 2-liter reaction vessel at a temperature of 70° C. The syrup was brought to the boiling point using vacuum. Seeding (at 70° C., in a supersaturation of 1.20) was made to the boiling syrup with 0.01% seeds on DS.

Cooling program was started after seeding from 70° C. to 65° C. during 3 hours. At the same time, the seeded syrup was boiled under vacuum for 4.0 hours, last hour at 65° C. The mass looked white and full of crystals. The centrifuging yield after 4 hours boiling was 56.9% on DS and 58.0% on maltitol. The crystal size was 140–250 μm.

The mass was slowly cooled to 60° C. overnight. 22 hours after the seeding, the centrifuging without wash gave 98.4% on DS cake and 92.3% on DS run-off purity, which corresponds to a 67.4% maltitol yield. The crystal size was 150–250 μm.

The purity of the cake centrifuged with a 10% wash was 99.3% on DS. The content of the impurities was 0.7% maltotritol on DS. The colour of the cake was 10 ICUMSA. The moisture content of the dried crystals was 0 0.05%. DSC-gram showed one peak at 148.6° C.

In the following tables, Tables I and II show a summary of the boiling crystallization tests of Examples 2 and 3, and the combined boiling and cooling crystallization tests of examples 4 and 5, respectively.

Tables III to VI show a summary of the purity analysis results of Examples 2 to 5, respectively. In Tables III to VI:

mass 1=the crystal mass immediately after boiling mass 2=the crystal mass after 18 to 20 hours of mixing at 60° C.

cent cryst=centrifuged crystal sample immediately after boiling cent run-off=centrifugation run-off sample immediately after boiling cake 0% wash=sample of the centrifugation cake after 18 to 20 hours of mixing at 60° C., without wash, run-off 0% wash=sample of the centrifugation run-off after 18 to 20 hours of mixing at 60° C., without wash cake 10% wash=sample of the centrifugation cake after 18 to 20 hours of mixing and washing with 10% water run-off 10% wash=sample of the centrifugation run-off after 18 to 20 hours of mixing and washing with 10% water.

measured with coulometric Karl Fischer titration.

TABLE I

Maltitol boiling crystallizations

| | Feed purity | | | Seeding | | After boiling | | | Centrifuging without wash | | | | | | | | Dried crystals, 10% wash | |
| | | | | | | | | | After boiling | | | | Overnight | | | | | |
| | | | | | | | | | Cake purity | | Yield | | Cake purity | | Yield | | DSC | |
| Ex. | Maltitol %/DS | Malto-tritol %/DS | Sorbitol %/DS | DS % | ss | DS % | ss | time h | Maltitol %/DS | Malto-tritol %/DS | DS % | M/M % | Maltitol %/DS | Malto-tritol %/DS | DS % | M/M % | Mois-ture % | Peak at C. |
| 2 | 95.7 | 2.3 | 1.5 | 77.2 | 1.15 | 88.3 | 1.30 | 3.0 | 98.2 | 1.1 | 68.6 | 70.4 | 98.6 | 1.0 | 65.6 | 67.5 | 0.07 | 148.8 |
| 3 | 96.5 | 2.7 | 0.5 | 77.1 | 1.15 | 89.2 | 1.59 | 4.3 | 97.8 | 1.8 | 78.0 | 79.0 | 98.4 | 1.4 | 72.4 | 73.8 | 0.24 | 148.1 |

TABLE II

Maltitol boiling crystallizations with cooling

| | Feed purity | | | Seeding | | After boiling | | | Centrifuging without wash | | | | | | | | Dried crystals, 10% wash | |
|---|---|---|---|---|---|---|---|---|---|---|---|---|---|---|---|---|---|---|
| | | | | | | | | | After boiling | | | | Overnight | | | | | |
| | | | | | | | | | Cake purity | | Yield | | Cake purity | | Yield | | | |
| Ex. | Maltitol %/DS | Maltotritol %/DS | Sorbitol %/DS | DS % | ss | DS % | ss | time h | Maltitol %/DS | Maltotritol %/DS | DS % | M/M % | Maltitol %/DS | Maltotritol %/DS | DS % | M/M % | Moisture % | DSC Peak at °C |
| 4 | 95.7 | 2.3 | 1.5 | 80.0 | 1.21 | 88.1 | 1.41 | 2.3 | 98.1 | 1.1 | 65.8 | 67.4 | 98.5 | 0.9 | 61.0 | 62.7 | 0.05 | 149.3 |
| 5 | 96.4 | 2.7 | 0.5 | 79.9 | 1.20 | 88.3 | 1.66 | 4.0 | 98.3 | 1.5 | 56.9 | 58.0 | 98.4 | 1.2 | 66.1 | 67.4 | 0.05 | 148.6 |

TABLE III

Analysis results (Example 2)

| | Samples | | | Carbohydrates HPLC | | Calculated |
|---|---|---|---|---|---|---|
| Number | Sample name | DS(KF) w - % | Colour ICUMSA | % on D.S. (KF) Maltotritol | Sorbitol | Maltitol % |
| 1 | Feed | 72.9 | 19 | 2.3 | 1.5 | 95.7 |
| 2 | Mass 1 | 88.3 | | | | |
| 3 | Cent cryst | 100.2 | | 1.1 | 0.5 | 98.2 |
| 4 | Cent run-off | 79.4 | | 4.1 | 3.2 | 91.4 |
| 5 | Mass 2 | 89.0 | | | | |
| 6 | Cake 0% wash | 99.5 | <10 | 1.0 | 0.4 | 98.6 |
| 7 | Run-off 0% wash | 78.3 | 57 | 4.7 | 3.5 | 90.6 |
| 8 | Cake 10% wash | 98.9 | <10 | 0.6 | 0.0 | 99.4 |
| 9 | Run-off 10% wash | 66.8 | 50 | 4.4 | 3.3 | 91.1 |
| 10 | Dried cryst 10% wash | 99.0* | 3 | 0.6 | 0.2 | 99.2 |

TABLE IV

Analysis results (Example 3)

| | Samples | | | Carbohydrates HPLC | | Calculated |
|---|---|---|---|---|---|---|
| Number | Sample name | DS(KF) w - % | Colour ICUMSA | % on D.S. (KF) Maltotritol | Sorbitol | Maltitol % |
| 1 | Feed | 68.4 | 23 | 2.7 | 0.5 | 96.5 |
| 2 | Mass 1 | 89.2 | | | | |
| 3 | Cent cryst | 100.1 | 8 | 1.8 | 0.3 | 97.8 |
| 4 | Cent run-off | 82.2 | 61 | 4.5 | 1.0 | 94.1 |
| 5 | Mass 2 | 89.7 | | | | |
| 6 | Cake 0% wash | 97.0 | 9 | 1.4 | 0.2 | 98.4 |
| 7 | Run-off 0% wash | 78.5 | 86 | 6.4 | 1.3 | 91.6 |
| 8 | Cake 10% wash | 96.3 | 5 | 1.4 | 0.2 | 98.3 |
| 9 | Run-off 10% wash | 59.7 | 76 | 5.9 | 1.2 | 92.2 |
| 10 | Dried cryst 10% wash | 99.8* | 10 | 1.3 | 0.2 | 98.5 |

TABLE V

Analysis results (Example 4)

| | Samples | | | Carbohydrates HPLC | | Calculated |
|---|---|---|---|---|---|---|
| Number | Sample name | DS(KF) w - % | Colour ICUMSA | % on D.S. (KF) Maltotritol | Sorbitol | Maltitol % |
| 1 | Feed | 68.6 | 20 | 2.3 | 1.5 | 95.7 |
| 2 | Mass 1 | 88.1 | | | | |
| 3 | Cent cryst | 100.0 | | 1.1 | 0.5 | 98.1 |
| 4 | Cent run-off | 81.6 | | 3.3 | 2.6 | 93.2 |
| 5 | Mass 2 | 88.1 | | | | |
| 6 | Cake 0% wash | 99.2 | <10 | 0.9 | 0.4 | 98.5 |
| 7 | Run-off 0% wash | 78.5 | 52 | 4.3 | 3.2 | 91.4 |
| 8 | Cake 10% wash | 100.0 | <10 | 0.5 | 0.1 | 99.4 |
| 9 | Run-off 10% wash | 71.9 | 42 | 3.9 | 2.8 | 92.3 |
| 10 | Dried cryst 10% wash | 100.0* | <10 | 0.5 | 0.0 | 99.5 |

TABLE VI

Analysis results (Example 5)

| | Samples | | | Carbohydrates HPLC | | Calculated |
|---|---|---|---|---|---|---|
| Number | Sample name | DS(KF) w - % | Colour ICUMSA | % on D.S. (KF) Maltotritol | Sorbitol | Maltitol % |
| 1 | Feed | 65.3 | 32 | 2.8 | 0.5 | 96.4 |
| 2 | Mass 1 | 88.3 | | | | |
| 3 | Cent cryst | 100.4 | | 1.5 | 0.2 | 98.3 |
| 4 | Cent run-off | 83.6 | | 3.9 | 0.7 | 95.0 |
| 5 | Mass 2 | 88.5 | | | | |
| 6 | Cake 0% wash | 98.5 | 10 | 1.2 | 0.2 | 98.4 |
| 7 | Run-off 0% wash | 77.8 | 83 | 5.8 | 1.2 | 92.3 |
| 8 | Cake 10% wash | 98.7 | <10 | 0.7 | 0.0 | 99.3 |
| 9 | Run-off 10% wash | 69.7 | 74 | 5.2 | 1.0 | 93.2 |

TABLE VI-continued

Analysis results (Example 5)

| Samples | | | Carbohydrates HPLC | | Calculated |
|---|---|---|---|---|---|
| Number | Sample name | DS(KF) w - % | Colour ICUMSA | % on D.S. (KF) Maltotritol Sorbitol | | Maltitol % |
| 10 | Dried cryst 10% wash | 100.0* | <10 | 0.7 | 0.0 | 99.3 |

EXAMPLE 6

Pilot Scale Crystallization (A) Boiling Crystallization

A total of 213 kg of dry substance of ion-exchanged maltitol syrup (RDS of 63.2%) was used as the feed syrup. The feed syrup had a maltitol content of 93.3%, a sorbitol content of 3.0% and a maltose content of 0.1% on RDS. In addition, the feed syrup contained 0.4% maltotritol (analyzed with HPLC Na$^+$column).

The syrup was evaporated at 60° C. to the seeding point. The boiling liquid was seeded with 80 g milled maltitol at RDS of 78.2%, at a temperature of 60.2° C. and in a supersaturation of 1.19. After seeding, the boiling crystallizaton was continued for 4.3 hours at 60° C. to RDS of 89.9%. The crystal size after boiling was about 100 μm. After the boiling, the mass was divided into two crystallizers.

(B1) Boiled Mass at a Constant Temperature of 60° C. Overnight

A part of the mass was moved to a 400-liter crystallizer which had been heated to a temperature of 60° C. The mass was kept at the constant temperature of 60° C. overnight. Crystallization yield was 65% on DS and 70% on maltitol. The crystal size was 100 to 200 μm.

Centrifugation tests of the mass were made using a laboratory centrifuge (basket diameter of 23 cm). The centrifugation tests were made after 21 hours from seeding. The maltitol content of the centrifugation cake without wash was 99.7% on RDS and the yield 66.9% on RDS. With 10% wash, the maltitol content of the cake was 99.1% on RDS and the yield was 56.7% on RDS.

Then three centrifugations were made with a pilot centrifuge (basket diameter of 40 cm) to obtain a maltitol cake for fluid bed drying tests. The maltitol content of the cake with three washings of 2.5 seconds was 99.6% on RDS.

(B2) Cooling of the boiled mass in a 10-liter crystallizer

The rest of the boiled mass from step (A) was put into a 10-liter cooling crystallizer. The mass was cooled linearly from 60° C. to 50° C. during 17 hours. The crystallization yield was 71.6% on DS and 76.7% on maltitol. The crystal size was 100 to 200 μm.

After cooling, the centrifugation tests of the mass were made using a laboratory centrifuge (basket diameter of 23 cm). The centrifugation tests were made after 28 hours from seeding. The maltitol content of the centrifugation cake without wash was 97.4% on RDS and the yield was 73.5% on RDS. With 10% wash, the maltitol content of the cake was 98.6% on RDS and the yield was 62.2% on RDS.

(C) Drying of the Crystals 1 kg of maltitol crystals (assay of 99.6% on RDS) was dried using an aeromatic fluid bed dryer, which is a typical laboratory fluid bed dryer where the air volume and temperature can be adjusted. After drying at 55° C., the moisture content was 0.08%. DSC showed a peak at 150.3° C.

Table VII shows a summary of the analysis results of Example 6.

TABLE VII

Analysis results (Example 6)

| Sample Name | RDS w - % | ICUMSA | Carbohydrates HPLC:Pb$^{2+}$ | | |
|---|---|---|---|---|---|
| | | | maltose % /RDS | maltitol % /RDS | sorbitol % /RDS |
| Feed | 63.2 | 1 | 0.1 | 93.3 | 3.0 |
| Seeding | 78.2 | | | | |
| Mass immediately after boiling | 89.9 | | | | |
| Mass before centrifuging | 90.3 | | | | |
| Cake 0% wash (B1) | 99.4 | 4 | 0.1 | 99.7 | 0.5 |
| Run-off 0% wash (B1) | 78.5 | 10 | 0.3 | 81.5 | 8.3 |
| Cake 10% wash (B1) | 99.6 | 0 | 0.1 | 99.1 | 0.1 |
| Run-off 10% wash (B1) | 70.6 | 10 | 0.3 | 83.4 | 7.1 |
| Cake 3 × 2.5 s wash (B1) | 97.6 | 1 | 0.1 | 99.6 | 0.0 |
| Run-off 3 × 2.5 s wash (B1) | 71.8 | 11 | 0.3 | 85.2 | 5.9 |
| Cake 0% wash (B2) | 99.2 | 0 | 0.1 | 97.4 | 0.6 |
| Run-off 0% wash (B2) | 76.6 | 1 | 0.4 | 78.8 | 9.6 |
| Cake 10% wash (B2) | 99.2 | 0 | 0.1 | 98.6 | 0.2 |
| Run-off 10% wash (B2) | 66.7 | 6 | 0.3 | 83.7 | 7.9 |

The foregoing general discussion and experimental examples are only intended to be illustrative of the present invention, and not to be considered as limiting. Other variations within the spirit and scope of this invention are possible and will present themselves to those skilled in the art.

What is claimed is:

1. A method of crystallizing maltitol from a maltitol solution by supersaturating the solution in respect of maltitol and crystallizing the maltitol from the solution, comprising bringing the maltitol-containing solution to a supersaturated state, and subjecting the solution to crystallization by evaporation until a crystallization mass is obtained which has a crystal yield of 1 to 80% on maltitol, and a dry solids content over 50%.

2. A method as claimed in claim 1, wherein the maltitol-containing solution used as the starting material contains at least about 85% by weight, preferably at least about 88% by weight of maltitol on dissolved dry solids.

3. A method as claimed in claim 1, wherein the maltitol-containing solution used as the starting material has an oligosaccharide content of less than 4% by weight on dissolved dry solids.

4. A method as claimed in claim 1, wherein the maltitol-containing solution is brought to a supersaturated state by evaporation.

5. A method as claimed in claim 4, wherein the evaporation is carried out at the boiling point of the solution.

6. A method as claimed in claim 5, wherein the evaporation is carried out at a temperature of 50° to 100° C., preferably at 55° to 70° C.

7. A method as claimed in claim 4, wherein the evaporation is carried out to a dry solids content of 80 to 90% by weight.

8. A method as claimed in claim 1, wherein the solution which has been brought to a supersaturated state is seeded.

9. A method as claimed in claim 8, wherein seeding is carried out by adding 0.001 to 1% by weight of maltitol seed crystals to the maltitol solution, based on the maltitol of the crystallization mass.

10. A method as claimed in claim 8, wherein seeding is carried out without adding maltitol seed crystals.

11. A method as claimed in claim 8, wherein the supersaturation of the solution in respect of maltitol during the seeding is 1.05 to 1.3.

12. A method as claimed in claim 1, wherein the crystallization by evaporation is carried out at the boiling point of the solution.

13. A method as claimed in claim 12, wherein the crystallization by evaporation is performed at a temperature of 50 to 100° C., preferably at 55 to 70° C.

14. A method as claimed in claim 1, wherein the supersaturation of the solution in respect of maltitol during the crystallization is 1.05 to 1.3.

15. A method as claimed in claim 1, wherein the crystallization by evaporation is continued for 1 to 15 hours.

16. A method as claimed in claim 1, wherein additional feed liquid is added to the maltitol solution simultaneously with the crystallization by evaporation.

17. A method as claimed in claim 1, wherein the maltitol-containing solution is cooled simultaneously with the crystallization by evaporation.

18. A method as claimed in claim 17, wherein the maltitol-containing solution is cooled to a temperature which is 10 to 20° C. lower than the seeding temperature.

19. A method as claimed in claim 1, wherein the crystallization by evaporation is continued until a crystallization mass is obtained which has a crystal yield of 30 to 80% on maltitol.

20. A method as claimed in claim 19, wherein the crystallization by evaporation is continued until a crystallization mass is obtained which has a crystal yield of 50 to 80% on maltitol.

21. A method as claimed in claim 1, wherein the crystallization by evaporation is continued until a crystallization mass is obtained which has crystal yield of 65 to 70% on dry solids.

22. A method as claimed in claim 1, wherein when the crystallization by evaporation is terminated, the crystallization mass is mixed without cooling.

23. A method as claimed in claim 22, wherein mixing is carried out under atmospheric pressure.

24. A method as claimed in claim 22, wherein the mixing is carried out at a temperature of 50 to 100° C., preferably at 55 to 70° C.

25. A method as claimed in claim 22, wherein mixing is continued to 0.5 to 30 hours.

26. A method as claimed in claim 1, wherein after the crystallization by evaporation has been terminated, the crystallization mass is cooled to a temperature range of 70 to 20° C.

27. A method as claimed in claim 22, wherein after the mixing has been terminated, the crystallization mass is cooled to a temperature of 70 to 20° C.

28. A method as claimed in claim 26, wherein the crystallization mass is cooled to a temperature range of 50 to 30° C.

29. A method as claimed in claim 26, wherein the crystallization mass is cooled for 10 to 50 hours.

30. A method as claimed in claims 1, wherein the crystals are recovered by centrifugation.

* * * * *